US00PP33808P2

(12) United States Plant Patent
van den Hoogen

(10) Patent No.: US PP33,808 P2
(45) Date of Patent: Jan. 4, 2022

(54) ***VERONICA* PLANT NAMED 'ALLVNAV'**

(50) Latin Name: ***Veronica longifolia* x *Veronica spicata***
Varietal Denomination: Allvnav

(71) Applicant: Wilhelmus T. J. van den Hoogen, Cuijk (NL)

(72) Inventor: Wilhelmus T. J. van den Hoogen, Cuijk (NL)

(73) Assignee: ALLPLANTS HOLDING B.V., Cuijk (NL)

( * ) Notice: Subject to any disclaimer, the term of this patent is extended or adjusted under 35 U.S.C. 154(b) by 0 days.

(21) Appl. No.: 17/151,491

(22) Filed: Jan. 18, 2021

(51) Int. Cl.
*A01H 5/02* (2018.01)
*A01H 6/68* (2018.01)

(52) U.S. Cl.
USPC ..... Plt./251
CPC ..... *A01H 6/68* (2018.05); *A01H 5/02* (2013.01)

(58) Field of Classification Search
USPC ..... Plt./251
CPC ..... A01H 6/68; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Veronica* plant named 'Allvnav', characterized by its upright plant habit with relatively long stems; dark green-colored leaves; freely flowering habit; dense and relatively long inflorescences with numerous violet blue-colored flowers; and good performance as a garden plant and as a cut flower.

2 Drawing Sheets

Figure 1:
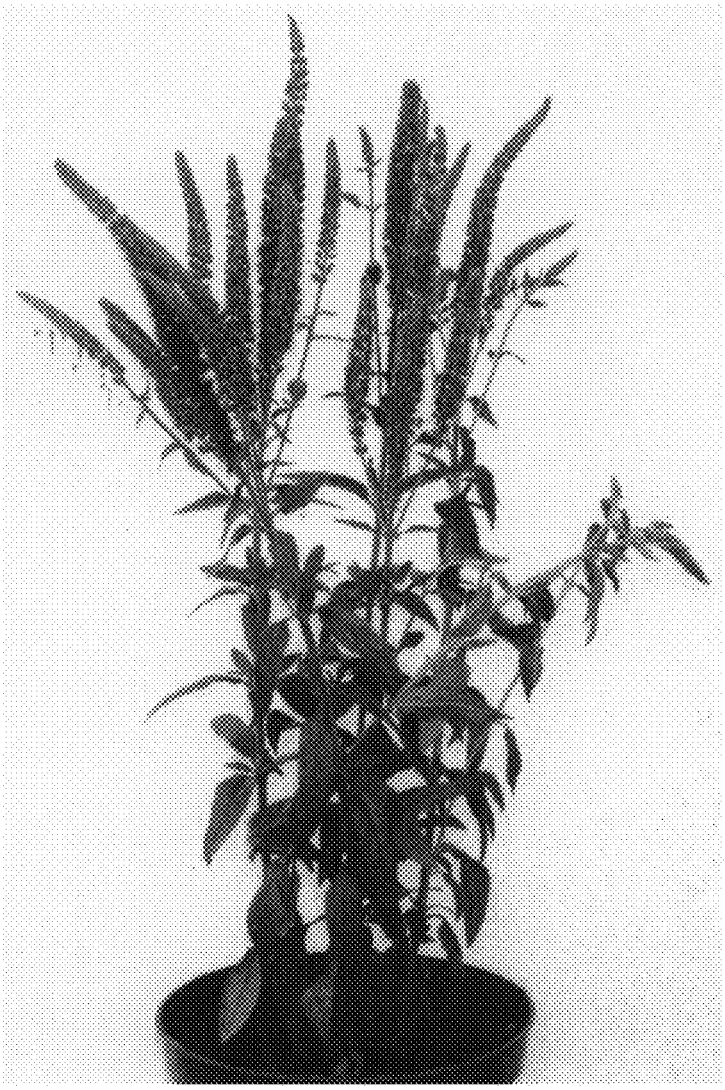

Botanical designation: *Veronica longifolia* x *Veronica spicata.*
Cultivar denomination: 'ALLVNAV'.

STATEMENT REGARDING PRIOR DISCLOSURES BY THE INVENTOR/APPLICANT & ASSIGNEE

An European Community Plant Breeder's Rights application for the instant plant was filed by the Assignee, All plants Holding B.V. of Cuijk, The Netherlands on Jan. 23, 2020, application number 2020/0211. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Veronica* plant, botanically known as *Veronica longifolia* x *Veronica spicata*, typically grown as a cut flower and hereinafter referred to by the name 'Allvnav'.

The new *Veronica* plant is a product of a planned breeding program conducted by the Inventor in Cuijk, The Netherlands. The objective of the breeding program is to create new attractive *Veronica* plants with long inflorescences with attractive flowers.

The new *Veronica* plant originated from an open-pollination in July, 2015 of a proprietary selection of *Veronica longifolia* x *Veronica spicata* identified as code number C14-3, not patented, as the female, or seed, parent with an unknown selection of *Veronica longifolia* x *Veronica spicata* as the male, or pollen, parent. The new *Veronica* plant was discovered and selected by the Inventor as a single flowering plant from within the progeny of the stated open-pollination in a controlled nursery environment in Cuijk, The Netherlands in July, 2016.

Asexual reproduction of the new *Veronica* plant by terminal stem cuttings in a controlled environment in Cuijk, The Netherlands, since September, 2016 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allvnav'. These characteristics in combination distinguish 'Allvnav' as a new and distinct *Veronica* plant:

1. Upright plant habit with relatively long stems.
2. Dark green-colored leaves.
3. Freely flowering habit.
4. Dense and relatively long inflorescences with numerous violet blue-colored flowers.
5. Good performance as a garden plant and as a cut flower.

Plants of the new *Veronica* differ primarily from plants of the female parent selection in the following characteristics:

1. Plants of the new *Veronica* have longer stems than plants of the female parent selection.
2. Plants of the new *Veronica* have thicker stems than plants of the female parent selection.

Plants of the new *Veronica* can be compared to plants of *Veronica longifolia* x *Veronica spicata* 'Alllaguna', disclosed in U.S. Plant Pat. No. 27,506. In side-by-side comparisons, plants of the new *Veronica* differ primarily from plants of 'Alllaguna' in the following characteristics:

1. Inflorescences of plants of the new *Veronica* do not express any deformities and are relatively straight whereas inflorescences of plants of 'Alllaguna' are typically fasciated and twisting.
2. Flowers of plants of the new *Veronica* are slightly lighter in color than flowers of plants of 'Alllaguna'.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet (FIG. 1) comprises a side perspective view of a typical flowering plant of 'Allvnav' grown in a container.

Figure 2:
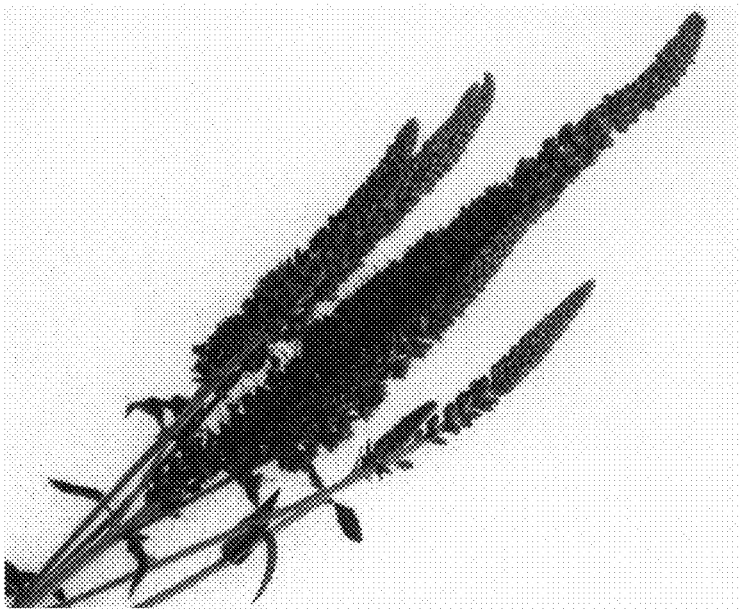
Figure 3:
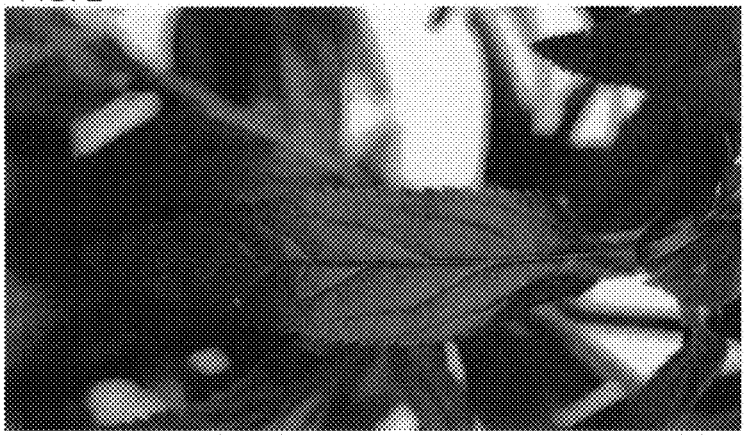

The photographs on the second sheet are close-up views of typical inflorescences (FIG. 2) and typical leaves (FIG. 3) of 'Allvnav'.

DETAILED BOTANICAL DESCRIPTION

Plants used for the aforementioned photographs and following description were grown in ground beds and in 20-cm containers during the summer in a shade-covered outdoor nursery in Naivasha, Kenya and under cultural practices typical of commercial *Veronica* production. During the production of the plants, day temperatures ranged from 23° C. to 28° C. and night temperatures ranged from 7° C. to 12° C. Plants were one year old when the photographs and the description were taken. In the following description, color references are made to The Royal Horticultural Society Colour Chart, 2015 Edition, except where general terms of ordinary dictionary significance are used.

Botanical classification: *Veronica longifolia* x *Veronica spicata* 'Allvnav'.

Parentage:

*Female, or seed, parent*.—Proprietary selection of *Veronica longifolia* x *Veronica spicata* identified as code number C14-3, not patented.

*Male, or pollen, parent*.—Unknown selection of *Veronica longifolia* x *Veronica spicata*, not patented.

Propagation:

*Type cutting*.—Terminal stem cuttings.

*Time to initiate roots, summer*.—About 10 to 14 days at temperatures ranging from 12° C. to 30° C.

*Time to produce a rooted young plant, summer*.—About 24 to 32 days at temperatures ranging from 12° C. to 30° C.

*Root description*.—Fine, fleshy; typically white in color, actual color of the roots is dependent on substrate composition, water quality, fertilizer type and formulation, substrate temperature and physiological age of roots.

*Rooting habit*.—Freely branching; dense.

Plant description:

*Plant type*.—Herbaceous perennial.

*Plant and growth habit*.—Upright plant habit with relatively long stems; overall plant shape, oblong; moderately vigorous growth habit and moderate growth rate.

*Plant height, soil level to top of foliar plane*.—About 57.3 cm.

*Plant height, soil level to top of floral plane*.—About 66.9 cm.

*Plant width*.—About 20.1 cm.

*Lateral branch description*.—Branching habit: Freely branching habit with about three main stems; pinching will enhance lateral branching. Length: About 41.5 cm. Diameter: About 4 mm. Internode length: About 4.5 cm. Strength: Strong. Aspect: About 7.5° from vertical. Texture and luster: Densely pubescent; slightly glossy. Color, developing and developed: Close to 144A.

Leaf description:

*Arrangement*.—Opposite or in whorls of three, simple.

*Length*.—About 6.8 cm.

*Width*.—About 2.4 cm.

*Shape*.—Narrowly ovate to lanceolate; slightly curled downward, very slightly carinate.

*Apex*.—Acute.

*Base*.—Truncate to very short attenuate.

*Margin*.—Serrate; not lobed.

*Texture and luster, upper surface*.—Moderately to densely pubescent; not rugose; slightly glossy.

*Texture and luster, lower surface*.—Mostly glabrous with exception of midvein which is densely pubescent; not rugose; matte.

*Venation pattern*.—Pinnate.

*Color*.—Developing leaves, upper surface: Close to 137A. Developing leaves, lower surface: Close to 138B. Fully expanded leaves, upper surface: Close to between NN137A and 147A; venation, close to 146B. Fully expanded leaves, lower surface: Close 147B; venation, close to 143B.

*Petioles*.—Length: About 1.1 cm. Diameter: About 2.5 mm by 3 mm. Strength: Strong. Texture and luster, upper and lower surfaces: Densely pubescent; slightly glossy. Color, upper surface: Close to 144B. Color, lower surface: Close to 144B; towards the margins, close to 144A.

Flower description:

*Flower arrangement and shape*.—Single campanulate flowers arranged on dense terminal compound racemes; flowers face mostly outwardly.

*Flowering habit*.—Freely flowering habit with about 1,800 flowers developing per inflorescence.

*Fragrance*.—None detected.

*Natural flowering season*.—Long flowering period; plants flower continuously from the summer until the autumn in The Netherlands.

*Flower longevity*.—Inflorescences last about 30 days on the plant and about 10 days as a cut flower; flowers not persistent.

*Flower buds*.—Length: About 5 mm. Diameter: About 2 mm. Shape: Elliptical. Texture and luster: Smooth, glabrous; matte. Color: Close to N88A; developing calyx, close to 143A.

*Inflorescence height (length)*.—About 22 cm.

*Inflorescence diameter*.—About 7.5 cm.
*Flower diameter*.—About 6 mm by 7 mm.
*Flower height*.—About 9 mm.
*Throat diameter*.—About 3.5 mm.
*Tube length*.—About 2 mm.
*Tube diameter*.—About 2.5 mm.
*Petals*.—Quantity and arrangement: Four in a single whorl; upper petal slightly broader than the lateral and lower petals; petals fused about 40% of the petal length from the base. Length, all petals: About 5 mm. Width, upper petal: About 3 mm. Width, lateral and lower petals: About 2 mm. Shape, upper petal: Obovate; moderately concave. Shape, lateral and lower petals: Narrowly oblong; moderately concave. Apex, all petals: Obtuse. Margin, all petals: Entire; not undulate. Texture and luster, all petals, upper and lower surfaces: Smooth, glabrous; matte. Texture and luster, throat: Smooth, glabrous; matte. Texture and luster, tube: Densely pubescent; matte. Color, all petals: When opening, upper and lower surfaces: Close to N88A. Fully opened, upper and lower surfaces: Close to 90B; color does not change with development. Throat: Close to 90B; venation, close to 90B. Tube: Close to 90C and fading proximally to close to 155A; venation, close to 90C fading proximally to close to 155A.
*Sepals*.—Quantity and arrangement: Four arranged in a single whorl and fused at the base. Length: About 1 mm to 3 mm. Width: About 1.25 mm. Shape: Ovate to broadly deltoid. Apex: Acute to broadly acute. Base: Broadly cuneate, fused. Margin: Entire. Texture and luster, upper and lower surfaces: Smooth, glabrous; matte. Color: When opening, upper surface: Close to 143B. When opening, lower surface: Close to 143A. Fully opened, upper and lower surfaces: Close to 138A.
*Peduncles*.—Length, terminal peduncles: About 21.7 cm. Length, axillary peduncles: About 16.6 cm. Diameter, terminal and axillary peduncles: About 3 mm. Aspect, terminal peduncles: Upright. Aspect, axillary peduncles: About 20° from terminal peduncle axis. Strength, terminal and axillary peduncles: Strong. Texture and luster, terminal and axillary peduncles: Densely pubescent; slightly glossy. Color, terminal and axillary peduncles: Close to 144B.
*Pedicels*.—Length: About 1 mm. Diameter: About 0.5 mm. Aspect: About 60° from peduncle axis. Strength: Moderately strong. Texture and luster: Sparsely pubescent; slightly glossy. Color: Close to 197A.
*Reproductive organs*.—Stamens: Quantity per flower: Typically not observed, if present, one or two. Filament length: About 6 mm. Filament color: Close to N88B. Anther shape: Short oblong; dorsifixed. Anther size: About 1 mm by 0.5 mm. Anther color: Close to N92C. Pollen amount: Moderate. Pollen color: Close to 157A. Pistils: Quantity per flower: One. Pistil length: About 6.5 mm. Stigma diameter: About 2 mm. Stigma shape: Club-shaped. Stigma color: Close to N92C. Style length: About 6.25 mm. Style color: Close to N88A and fading proximally to close to N88C. Ovary color: Close to 145B.
*Seeds and fruits*.—To date, seed and fruit development has not been observed on plants of the new *Veronica*.

Pathogen & pest resistance: To date, plants of the new *Veronica* have not been noted to be resistant to pathogens and pests common to *Veronica* plants.

Garden performance: Plants of the new *Veronica* have exhibited good garden performance and to be tolerant to rain, wind, temperatures ranging from about −29° C. to about 35° C. and to be suitable for USDA Hardiness Zones 4 through 9.

It is claimed:

1. A new and distinct *Veronica* plant named 'Allvnav' as illustrated and described.

* * * * *